United States Patent
Zappala

(12) 
(10) Patent No.: US 6,569,161 B2
(45) Date of Patent: May 27, 2003

(54) RETRACTABLE RADIOFREQUENCY NEEDLE POINT ELECTRODE AND METHODS FOR USING SAME

(76) Inventor: Stephen M. Zappala, 98 Rattlesnake Hill Rd., Andover, MA (US) 01810

( * ) Notice: Subject to any disclaimer, the term of this patent is extended or adjusted under 35 U.S.C. 154(b) by 0 days.

(21) Appl. No.: 09/798,375

(22) Filed: Mar. 2, 2001

(65) Prior Publication Data

US 2001/0037107 A1 Nov. 1, 2001

Related U.S. Application Data

(60) Provisional application No. 60/186,453, filed on Mar. 2, 2000.

(51) Int. Cl.[7] .......................... A61B 17/00; A61B 18/18
(52) U.S. Cl. .................... 606/41; 606/45; 606/49; 607/98
(58) Field of Search .................. 606/39, 40, 41, 606/44, 45, 49; 607/98, 99

(56) References Cited

U.S. PATENT DOCUMENTS

| 4,043,342 A | * | 8/1977 | Morrison, Jr. ............... 606/48 |
| 5,281,218 A | * | 1/1994 | Imran ........................... 606/41 |
| 5,403,311 A | * | 4/1995 | Abele et al. .................. 606/49 |
| 5,437,662 A | * | 8/1995 | Nardella ....................... 606/40 |

* cited by examiner

*Primary Examiner*—Philip H. Leung
(74) *Attorney, Agent, or Firm*—Mirick, O'Connell, DeMallie & Lougee, LLP

(57) ABSTRACT

A surgical radiofrequency needle point electrode for delivering both coagulating and cutting currents, comprising, at least one housing member; at least one needle point electrode having a surgically active region that is adapted to deliver both coagulating and cutting currents; and a telescoping member for at least temporarily maintaining the surgically active region of the electrode in the housing member.

20 Claims, 2 Drawing Sheets

RETRACTABLE RADIOFREQUENCY NEEDLE POINT ELECTRODE AND METHODS FOR USING SAME

CROSS-REFERENCE

This application claims the benefit of the filing date of provisional application Ser. No. 60/186,453 filed on Mar. 2, 2000.

FIELD OF THE INVENTION

The invention relates to devices for electrosurgery and more specifically to a retractable needle point electrode device for coagulating and cutting that reduces the risk of injury to patients and medical personnel, and methods for using the device.

BACKGROUND OF THE INVENTION

Radiofrequency (RF) is commonly employed in electrosurgery through a hand held activator, which delivers both coagulating and cutting currents. The terminal section of the hand held delivery system applies the RF through a detachable stainless steel electrode at the tip. Electrodes are available in many shapes and sizes. The tips used for conventional surgery are either blunt or needle point. The needle point electrode offers significant advantages over larger and/or blunt tipped electrodes. The fine point of the needle improves accuracy to dessicate, diminishes RF scattering during coagulation and increases the versatility of electrosurgery, especially within the pediatric surgical population. Moreover, the widespread acceptance of minimally invasive surgical techniques and laparoscopy will usher in wider applications for needle tip delivery systems.

However, needle point electrodes have several drawbacks. Significant morbidity to both the patient and the entire surgical team is associated with the needle point electrode. The needle point is sharp enough to penetrate a vital organ or major vascular structure if inadvertently dropped into an open incision. The surgeon and allied health personnel are also at significant risk for puncture wounds during surgical procedures. As such, in view of the further risk of contracting HIV and Hepatitis viruses through such puncture wounds, many operating rooms avoid using the needle point system.

There are devices known that include either retractable electrodes, such as the jaw-like retractable blades disclosed in U.S. Pat. No. 5,456,684 and the complex retractable, adjustably angled needle point devices disclosed in U.S. Pat. Nos. 5,366,490 and 5,456,684. However, these devices are limited to very specific uses, they are complex and are not adapted for delivering finely directed and easily manipulated currents for both coagulation and cutting.

SUMMARY OF THE INVENTION

It is therefore a primary object of this invention to provide a surgical electrode that is accurate, versatile and safe, and to provide methods for using the electrode.

It is a further object of this invention to provide a safe, surgical electrode that is particularly suited for use within the pediatric surgical population.

It is a further object of this invention to provide a retractable needle point electrode that is adapted to deliver coagulating and cutting currents.

It is a further object of this invention to provide a retractable needle point electrode that is disposable and enhances the safety of electrosurgery to both personnel and patients.

A preferred embodiment of the surgical radiofrequency needle point electrode of the invention generally comprises: at least one housing member; at least one needle point electrode having a surgically active region that is adapted to deliver both coagulating and cutting currents; and a means for at least temporarily maintaining said surgically active region of said electrode in said housing member. The means for maintaining preferably comprises one or more telescoping members. The device may also comprise a means for deploying said surgically active region of said electrode out of said housing member, wherein said means for deploying preferably comprises one or more tension spring members. The device may still further comprise a means for retracting said surgically active region of said electrode into said housing member, wherein the one or more telescoping members are preferably utilized as both the means for maintaining and the means for retracting.

The method of the invention for using a surgical radiofrequency needle point electrode, generally comprises the steps of: providing a surgical radio frequency electrode device comprising, at least one housing member; at least one needle point electrode having a surgically active region that is adapted to deliver both coagulating and cutting currents; a means for maintaining said surgically active region of said electrode in said housing member; and a means for deploying said surgically active region of said electrode from said housing member; deploying said surgically active region of said electrode from said housing into one or more surgical positions; and activating said surgically active region of said electrode. The means of the device for deploying preferably comprises one or more tension spring members. The method may further comprise a step of retracting said surgically active region of said electrode into said housing member, wherein said device further comprises a means for retracting said surgically active region of said electrode into said housing member, wherein said means for retracting preferably comprises one or more tension spring members.

The invention is the result of efforts to design an insulated needle adapted to deliver radiofrequency current at its tip and that can be completed retracted within a hand held activator in a manner similar to a ball point pen wherein the needle tip is exposed by manually depressing an activation switch. The needle may be retracted by pressing the tip of the needle against a pad to cause the needle to telescope back into the activator housing.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS AND METHODS

Figure 1:
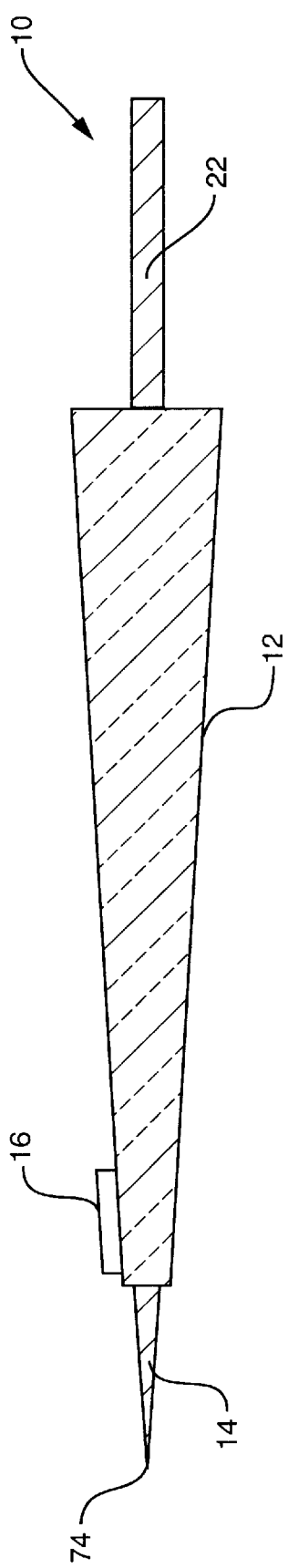
FIG. 1 is a side view of the preferred embodiment of the device of the invention.
Figure 2:
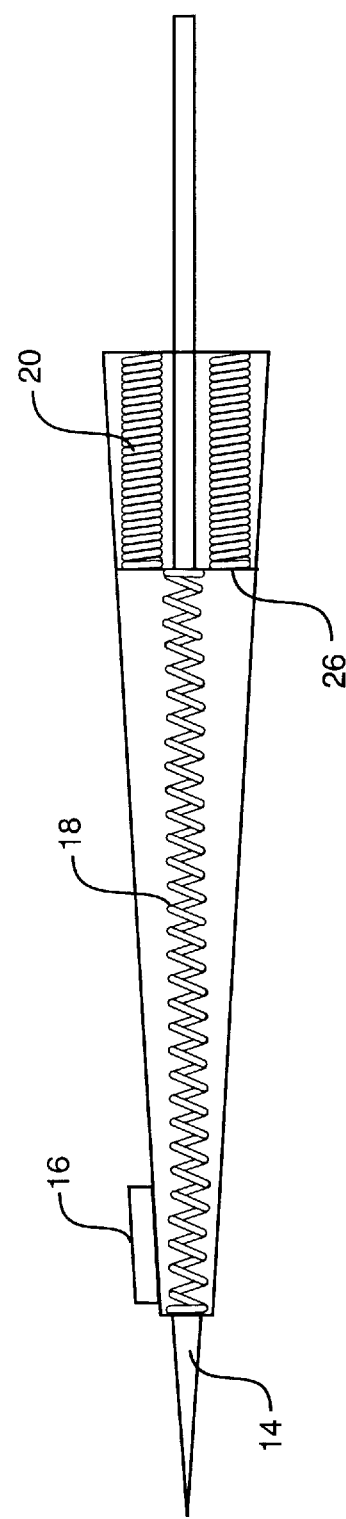
FIG. 2 is a cross-sectional side view of the preferred embodiment shown in FIG. 1 with the needle point in the deployed surgical position.
Figure 3:
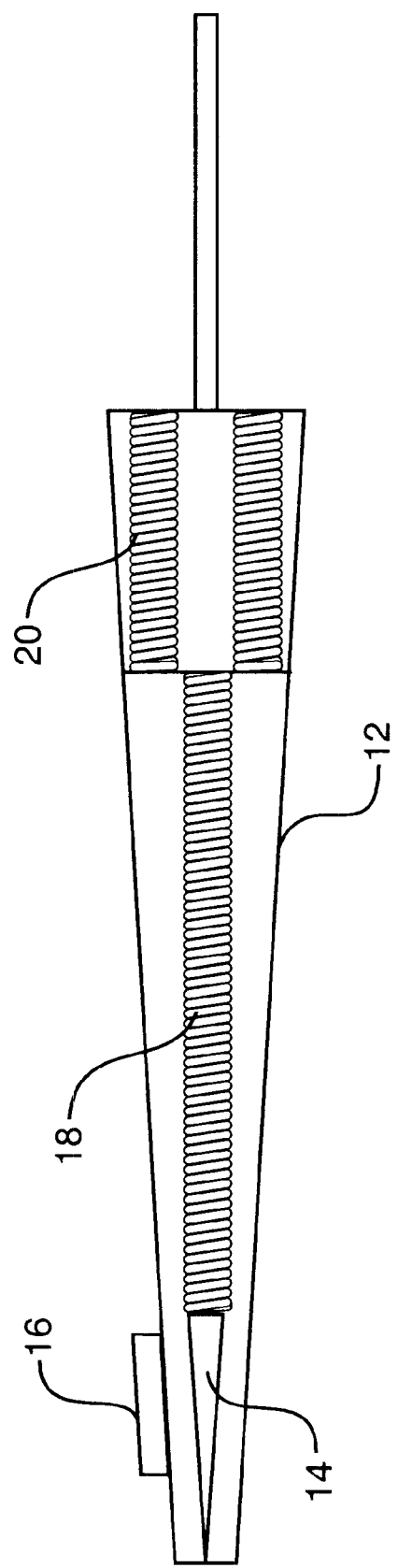
FIG. 3 is a cross-sectional side view of the preferred embodiment shown in FIG. 1 with the needle point retracted within the housing in a storage or stand-by position.

The invention generally features a needle point electrode, adapted for coagulating and cutting, that is deployed from, retracted into, and maintained within, a housing. The preferred embodiment of the device of the invention is shown in FIGS. 1–3 and is generally referred to as device 10. Device 10 is designed to be readily inserted into currently available hand held systems connected to a generator and disposed of after a single use.

Device 10 includes at least one housing member 12; at least one needle point electrode 14 having a surgically active region 24 that is adapted to deliver both coagulating and cutting currents; and a means for at least temporarily maintaining said surgically active region of said electrode in said housing member. The means for maintaining preferably comprises one or more telescoping members 18. In device 10, the telescoping member comprises spring 18 which places backward pressure against the inside distal surface of housing 12. The device may also comprise a means for deploying said surgically active region of said electrode out of said housing member, wherein said means for deploying preferably comprises one or more tension spring members 20 and switch 16. Tension spring member 20 places forward pressure against pressure member 26. The device may still further comprise a means for retracting said surgically active region of said electrode into said housing member, wherein the one or more telescoping members are utilized to retract and maintain the needle tip in the housing.

Device 10 is preferably insulated over 80% of its electrode surface to reduce scatter and the inadvertent delivery of current through tissue that may come into contact with the shaft of device 10.

The method of the invention for using a surgical radiofrequency needle point electrode begins by providing a surgical radio frequency electrode device, such as device 10, and inserting device 10 into a hand held device that is connected to an RF generator. The surgically active region of needle point electrode is then deployed from housing 12 by compressing or otherwise activating switch 24 so that the surgically active tip of electrode 14 is in a suitable surgical position. Once in position, the surgically active region is activated by initiating a current for cutting and/or coagulating through the electrode. After the tissues are cut, ablated and/or coagulated as needed, the surgically active region of the needle point electrode is preferably retracted back into the housing member by pressing the tip of the needle against a surface to cause the needle and insulating shaft to telescope back into a standby or safe deployment position as shown in FIG. 3. A rectangular or other suitably shaped pad, preferably with a hard plastic disc at its center, is used to provide the firm surface necessary for needle tip depression.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A surgical radiofrequency needle point electrode for delivering both coagulating and cutting currents, comprising,
    at least one housing member;
    at least one needle point electrode having a surgically active region that is adapted to deliver both coagulating and cutting currents; and
    a means for at least temporarily maintaining said surgically active region of said electrode in said housing member.

2. The device of claim 1, wherein said means for maintaining comprises one or more telescoping members.

3. The device of claim 1, further comprising a means for deploying said surgically active region of said electrode out of said housing member.

4. The device of claim 3, wherein said means for deploying comprises one or more tension spring members.

5. The device of claim 1, further comprises a means for retracting said surgically active region of said electrode into said housing member.

6. The device of claim 5, wherein said means for retracting comprises one or more telescoping members.

7. The needle point electrode device of claim 1, wherein said needle point electrode has an electrode surface that is insulated over 80% of its electrode surface.

8. A method for using a surgical radiofrequency needle point electrode, comprising the steps of,
    providing a surgical radio frequency electrode comprising,
        at least one housing member;
        at least one needle point electrode having a surgically active region adapted to deliver both coagulating and cutting currents;
    a means for maintaining said surgically active region of said electrode in said housing member; and
    a means for deploying said surgically active region of said electrode from said housing member;
    deploying said surgically active region of said electrode from said housing into one or more surgical positions; and
    activating said surgically active region of said electrode.

9. The method of claim 8, wherein said means for deploying comprises one or more tension spring members.

10. The method of claim 8, further comprising a step of retracting said surgically active region of said electrode into said housing member, wherein said device further comprises a means for retracting said surgically active region of said electrode into said housing member.

11. The method of claim 10, wherein said means for retracting comprises one or more tension spring members.

12. A surgical radiofrequency needle point electrode device for delivering all three coagulating, cutting and ablating currents, comprising,
    at least one housing member;
    at least one needle point electrode, adapted for pediatric applications, having a surgically active region that is adapted to deliver all three coagulating, cutting and ablating currents; and
    a means for at least temporarily maintaining said surgically active region of said electrode in said housing member.

13. The needle point electrode device of claim 12, further comprising a means for at least temporarily deploying said surgically active region of said electrode out of said housing member, wherein said means for at least temporarily maintaining said surgically active region of said electrode in said housing member comprises a first tension spring member that places backward pressure against an inside distal surface of said housing member; and wherein said means for at least temporarily deploying said surgically active region of said electrode out of said housing member comprises a second tension spring member that places forward pressure against an inside proximal surface of said housing member.

14. The needle point electrode device of claim 13, further comprising a means for retracting said surgically active region of said electrode into said housing member.

15. The needle point electrode device of claim 14, wherein said means for retracting comprises one or more telescoping members.

16. The needle point electrode device of claim 12, further comprising a means for deploying said surgically active region of said electrode out of said housing member.

17. The needle point electrode device of claim 16, further comprising a means for retracting said surgically active region of said electrode into said housing member.

18. The needle point electrode device of claim 17 wherein said needle point electrode has an electrode surface that is insulated over 80% of its electrode surface.

19. The needle point electrode device of claim 12, further comprising a means for retracting said surgically active region of said electrode into said housing member.

20. The needle point electrode device of claim 18, wherein said needle point electrode has an electrode surface that is insulated over 80% of its electrode surface.

* * * * *